(12) United States Patent
Chadeayne

(10) Patent No.: US 11,358,934 B2
(45) Date of Patent: Jun. 14, 2022

(54) CRYSTALLINE FORMS OF PSILACETIN

(71) Applicant: CAAMTECH LLC, Issaquah, WA (US)

(72) Inventor: Andrew R. Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 275 days.

(21) Appl. No.: 16/827,075

(22) Filed: Mar. 23, 2020

(65) Prior Publication Data

US 2021/0292278 A1    Sep. 23, 2021

(51) Int. Cl.
*A61K 31/4045* (2006.01)
*C07D 209/16* (2006.01)
*A61K 36/185* (2006.01)

(52) U.S. Cl.
CPC ........ *C07D 209/16* (2013.01); *A61K 31/4045* (2013.01); *A61K 36/185* (2013.01); *C07B 2200/13* (2013.01)

(58) Field of Classification Search
CPC .................................................. C07B 2200/13
See application file for complete search history.

(56) References Cited

U.S. PATENT DOCUMENTS

| 2018/0221396 A1 | 8/2018 | Chadeayne |
| 2019/0142851 A1 | 5/2019 | Chadeayne |

OTHER PUBLICATIONS

Palma et al., An old chemical that became a new psychoactive substance: Study on O-Acetylpsilocin samples handled for analysis and raise of awareness. European Neuropsychopharmacology, (Sep. 2015) vol. 25, Supp. Suppl. 2, pp. S620-S621. Abstract No. P.6.d. 016 (Year: 2015).*
Chadeayne, Bis(4-acet-oxy-N,N-di-methyl-tryptammonium) fumarate: a new crystalline form of psilacetin, an alternative to psilocybin as a psilocin prodrug. Acta crystallographies. Section E, Crystallographic communications, (Jun. 1, 2019) vol. 75, No. Pt 6, pp. 900-902 (Year: 2019).*
Carhart-Harris, R. L.; Goodwin, G. M. "The Therapeutic Potential of Psychedelic Drugs: Past, Present, and Future" Neuropsychopharmacology, 2017, 42, 2105-2113.
Chadeayne, A. R., Golen, J. A. & Manke, D. R. (2019). Psychedelic Science Review, https://psychedelicreview.com/the-crystal-structure-of-4-aco-dmt-fumarate/.
Dinis-Oliveira, R. J. (2017). Drug Metab. Rev. 49, 84-91.
Dolomanov, O. V.; Bourhis, L. "OLEX2: a complete structure solution, refinement and analysis program" Journal of Applied Crystallography, 2009, 42, 339-341.
Gilman, A.; Hardman, J.; Limbird L., eds., Goodman and Gilman's "The Pharmacological Basis of Therapeutics," Tenth Edition, McGraw-Hill Press, 155-173 (2001).
Nichols, D. E.; Frescas, S. "Improvements to the Synthesis of Psilocybin and a Facile Method for Preparing the OAcetyl Prodrug of Psilocin" Synthesis, 1999, 6, 935-938.
Petcher, T. J.; Weber, H. P. "Crystal Structure of the Teonanácatl Hallucinogens. Part II. Psilocin, C12H15N2O" Journal of the Chemical Society, Perkins Transactions II, 1974, 946-948.
Weber, H. P.; Petcher, T. J. "Crystal Structure of the Teonanacatl Hallucinogens. Part I. Psilocybin C12H17N2O4P" Journal of the Chemical Society, Perkins Transactions II, 1974, 942-946.

* cited by examiner

Primary Examiner — Qiuwen Mi
(74) Attorney, Agent, or Firm — J.A. Lindeman & Co. PLLC

(57) ABSTRACT

Crystalline forms of 4-acetoxy-N,N-dimethyltryptamine (psilacetin), compositions containing that crystalline form, and their methods of use are disclosed. The crystalline forms of 4-acetoxy-N,N-dimethyltryptamine (psilacetin) according to the disclosure include crystalline 4-acetoxy-N,N-dimethyltryptammonium hydrofumarate, the fumarate salt of psilacetin, and/or crystalline bis(4-acetoxy-N,N-dimethyltryptammonium) fumarate, and pharmaceutical compositions containing a crystalline form of psilacetin.

11 Claims, 7 Drawing Sheets

CRYSTALLINE FORMS OF PSILACETIN

TECHNICAL FIELD

This disclosure relates to crystalline forms of 4-acetoxy-N,N-dimethyltryptamine (psilacetin), compositions containing that crystalline form, and methods of using the same. The crystalline forms of 4-acetoxy-N,N-dimethyltryptamine (psilacetin) according to the disclosure include crystalline 4-acetoxy-N,N-dimethyltryptammonium hydrofumarate, the fumarate salt of psilacetin, and/or crystalline bis(4-acetoxy-N,N-dimethyltryptammonium) fumarate, and pharmaceutical compositions containing a crystalline form of psilacetin.

BACKGROUND

Psychedelic agents have received a great deal of interest lately as potential pharmaceuticals to treat mood disorders, including depression and post-traumatic stress disorder (PTSD) (Carhart-Harris & Goodwin, 2017). Psilocybin, a naturally occurring tryptamine derivative found in 'magic' mushrooms, is a prodrug of psilocin. When consumed orally, psilocybin hydrolyzes to generate psilocin, a serotonin-2a agonist, producing mood-altering or 'psychedelic' effects (Dinis-Oliveira, 2017). Like psilocybin, psilacetin serves as a prodrug of psilocin. Psilactin, 4-acetoxy-N,N-dimethyltryptamine, commonly 4-AcO-DMT, is the O-acetyl prodrug of psilocin. Compared to psilocybin, psilacetin is easier and less expensive to synthesize. This suggests that administering psilacetin (instead of psilocybin) represents a better means of delivery for the active psilocin. Psilacetin was first reported in 1999 by Nichols and co-workers (Nichols & Frescas, 1999), generally producing the molecule as its crystalline fumarate salt. However, until the work disclosed herein, no work has been done to develop particular crystalline forms of psilacetin or its salts.

SUMMARY OF THE DISCLOSURE

The disclosure relates to new crystalline forms of 4-acetoxy-N,N-dimethyltryptamine (psilacetin), specifically crystalline 4-acetoxy-N,N-dimethyltryptammonium hydrofumarate, the fumarate salt of psilacetin or crystalline bis(4-acetoxy-N,N-dimethyltryptammonium) fumarate, and to pharmaceutical compositions containing a crystalline form of psilacetin. Bis(4-acetoxy-N,N-dimethyltryptammonium) fumarate is itself a novel compound.

In one embodiment, 4-acetoxy-N,N-dimethyltryptammonium hydrofumarate according to the disclosure is characterized by a monoclinic, $P2_1/c$ crystal system space group at a temperature of about 296 K; unit cell dimensions a=13.023 (1) Å, b=7.4823 (6) Å, c=19.102 (2) Å, α=90°, β=103.251 (3 103.251 (3)°, and γ=90° at a temperature of about 296 K; an x-ray powder diffraction pattern substantially similar to FIG. 4; or an x-ray powder diffraction pattern characterized by peaks at 7.0, 13.0 and 21.8°2θ±0.2°2θ.

In one embodiment, crystalline bis(4-acetoxy-N,N-dimethyltryptammonium) fumarate according to the disclosure is characterized by a triclinic, P1 crystal system space group at a temperature of about 200 K; unit cell dimensions a=8.3965 (13) Å, b=8.9879 (14) Å, c=12.0126 (16) Å, α=101.730 (5)°, β=100.818 (5)°, and γ=112.463 (5)° at a temperature of about 200 K; an x-ray powder diffraction pattern substantially similar to FIG. 8; or an x-ray powder diffraction pattern characterized by peaks at 7.9, 18.4 and 24.0°2θ±0.2°2θ.

The disclosure also relates to compositions comprising a crystalline form of 4-acetoxy-N,N-dimethyltryptamine (psilacetin), specifically crystalline 4-acetoxy-N,N-dimethyltryptammonium hydrofumarate, the fumarate salt of psilacetin or crystalline bis(4-acetoxy-N,N-dimethyltryptammonium) fumarate, and to pharmaceutical compositions containing a crystalline form of psilacetin and an excipient.

The disclosure also relates to compositions comprising a combination of, as a first component, a crystalline form of 4-acetoxy-N,N-dimethyltryptamine (psilacetin), specifically crystalline 4-acetoxy-N,N-dimethyltryptammonium hydrofumarate, the fumarate salt of psilacetin or crystalline bis (4-acetoxy-N,N-dimethyltryptammonium) fumarate, and a second component selected from (a) a purified psilocybin derivative, (b) one or two purified cannabinoids and (c) a purified terpene.

The disclosure further relates to methods of preventing or treating a physical and/or psychological disorder comprising the step of administering to a subject in need thereof an effective amount of a crystalline form of 4-acetoxy-N,N-dimethyltryptamine (psilacetin), specifically crystalline 4-acetoxy-N,N-dimethyltryptammonium hydrofumarate, the fumarate salt of psilacetin or crystalline bis(4-acetoxy-N,N-dimethyltryptammonium) fumarate, and to pharmaceutical compositions containing a crystalline form of psilacetin, or a composition according to the disclosure.

The disclosure also relates to methods of preventing or treating inflammation and/or pain comprising the step of administering to a subject in need thereof an effective amount of a crystalline form of 4-acetoxy-N,N-dimethyltryptamine (psilacetin), specifically crystalline 4-acetoxy-N,N-dimethyltryptammonium hydrofumarate, the fumarate salt of psilacetin or crystalline bis(4-acetoxy-N,N-dimethyltryptammonium) fumarate, and to pharmaceutical compositions containing a crystalline form of psilacetin, or a composition according to the disclosure.

DETAILED DESCRIPTION

Figure 1:
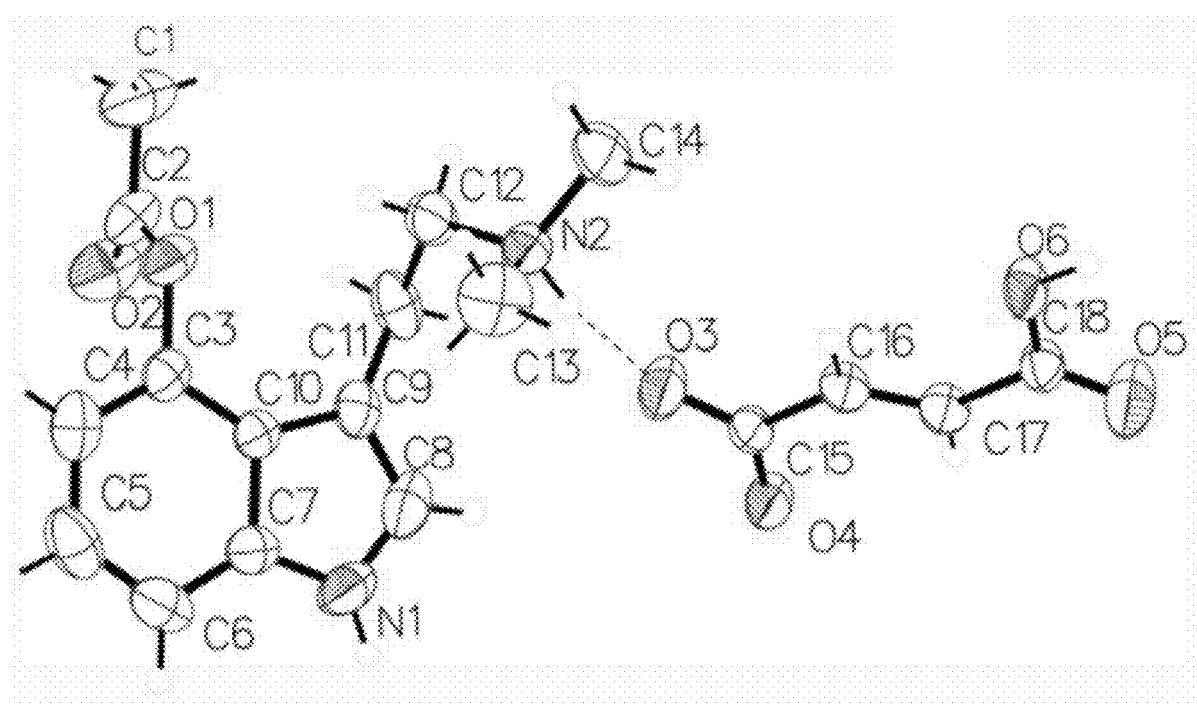
FIG. 1 shows the molecular structure of 4-acetoxy-N,N-dimethyltryptammonium hydrofumarate, the fumarate salt of psilacetin, with atoms labeled.

This disclosure relates to crystalline forms of 4-acetoxy-N,N-dimethyltryptamine (psilacetin), specifically crystalline 4-acetoxy-N,N-dimethyltryptammonium hydrofumarate, the fumarate salt of psilacetin or crystalline bis(4-acetoxy-N,N-dimethyltryptammonium) fumarate, and to pharmaceutical compositions containing a crystalline form of psilacetin according to the disclosure. The therapeutic uses of the crystalline forms of 4-acetoxy-N,N-dimethyltryptamine (psilacetin) according to the disclosure, are described below as well as compositions containing them. The crystalline forms of 4-acetoxy-N,N-dimethyltryptamine (psilacetin) according to the disclosure, and the methods used to characterize it are described in the example below.

Bis(4-acetoxy-N,N-dimethyltryptammonium) fumarate is itself a novel compound having the following structural formula:

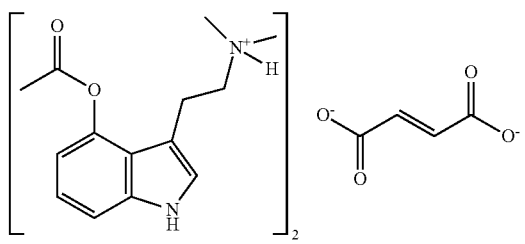

Bis{2-[4-(acetyloxy)-1H-indol-3-yl]ethan1-aminium}but-2-enedioate), $2C_{14}H_{19}N_2O_2+$ $C_4H_2O_4^{2-}$.

In one embodiment, bis(4-acetoxy-N,N-dimethyltryptammonium) fumarate has a single protonated psilacetin cation and one half of a fumarate dianion in the asymmetric unit. There are N—H - - - O hydrogen bonds between the ammonium H atoms and the fumarate O atoms, as well as N—H - - - O hydrogen bonds between the indole H atoms and the fumarate O atoms. The hydrogen bonds hold the ions together in infinite one-dimensional chains along [111]. See FIGS. 2 and 3.

Methods of Treatment and Therapeutic Uses

In one embodiment, the crystalline forms of 4-acetoxy-N,N-dimethyltryptamine (psilacetin) according to the disclosure, specifically crystalline 4-acetoxy-N,N-dimethyltryptammonium hydrofumarate, the fumarate salt of psilacetin or crystalline bis(4-acetoxy-N,N-dimethyltryptammonium) fumarate, the methods and the compositions, particularly the pharmaceutical compositions, of the disclosure are used to regulate the activity of a neurotransmitter receptor by administering a therapeutically effective dose of a crystalline form of psilacetin according to the disclosure. In another embodiment, the crystalline forms of 4-acetoxy-N,N-dimethyltryptamine (psilacetin) according to the disclosure, specifically crystalline 4-acetoxy-N,N-dimethyltryptammonium hydrofumarate, the fumarate salt of psilacetin or crystalline bis(4-acetoxy-N,N-dimethyltryptammonium) fumarate, the methods and the compositions, particularly the pharmaceutical compositions, of the disclosure are used to treat inflammation and/or pain by administering a therapeutically effective dose of a crystalline form of psilacetin according to the disclosure. Methods of the disclosure administer a therapeutically effective amount of a crystalline form of psilacetin according to the disclosure to prevent or treat a disease or condition, such as those discussed below for a subject in need of treatment. A crystalline form of psilacetin according to the disclosure may be administered neat or as a composition comprising a crystalline form of psilacetin according to the disclosure as discussed below.

A crystalline form of psilacetin according to the disclosure may be used to prevent and/or treat a psychological disorder. The disclosure provides a method for preventing and/or treating a psychological disorder by administering to a subject in need thereof a therapeutically effective amount of a crystalline form of psilacetin according to the disclosure, including the preferred embodiments discussed herein. The psychological disorder may be chosen from depression, psychotic disorder, schizophrenia, schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome, post-traumatic stress disorder (PTSD), premenstrual dysphoric disorder (PMDD), and premenstrual syndrome (PMS).

A crystalline form of psilacetin according to the disclosure may be used to prevent and/or treat of a brain disorder. The disclosure provides a method for preventing and/or treating a brain disorder by administering to a subject in need thereof a therapeutically effective amount of a crystalline form of psilacetin according to the disclosure, including the preferred embodiments discussed above. The brain disorder is chosen from Huntington's disease, Alzheimer's disease, dementia, and Parkinson's disease.

A crystalline form of psilacetin according to the disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of a crystalline form of psilacetin according to the disclosure, including the preferred embodiments discussed above.

A crystalline form of psilacetin according to the disclosure may be used to prevent and/or treat inflammation and/or pain, such as for example inflammation and/or pain associated with inflammatory skeletal or muscular diseases or conditions. The disclosure provides a method for preventing and/or treating a inflammation and/or pain by administering to a subject in need thereof a therapeutically effective amount of a crystalline form of psilacetin according to the disclosure, including the preferred embodiments discussed herein. Generally speaking, treatable "pain" includes nociceptive, neuropathic, and mix-type, A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e. mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendonopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibrornyalgia.

Compositions

The disclosure also relates to compositions comprising an effective amount of a crystalline form of psilacetin according to the disclosure, specifically crystalline 4-acetoxy-N,N-dimethyltryptammonium hydrofumarate, the fumarate salt of psilacetin or crystalline bis(4-acetoxy-N,N-dimethyltryptammonium) fumarate, especially pharmaceutical compositions comprising a therapeutically effective amount of a crystalline form of psilacetin according to the disclosure and a pharmaceutically acceptable carrier (also known as a pharmaceutically acceptable excipient). As discussed above, a crystalline form of psilacetin according to the disclosure may be, for example, therapeutically useful to prevent and/or treat the psychological and other disorders discussed above.

A composition or a pharmaceutical composition of the disclosure may be in any form which contains a crystalline form of psilacetin according to the disclosure. The composition may be, for example, a tablet, capsule, liquid suspension, injectable, topical, or transdermal. The compositions or pharmaceutical compositions generally contain, for example, about 1% to about 99% by weight of a crystalline form of psilacetin according to the disclosure and, for example, 99% to 1% by weight of at least one suitable pharmaceutical excipient. In one embodiment, the composition may be between about 5% and about 75% by weight of a crystalline form of psilacetin according to the disclosure with the rest being at least one suitable pharmaceutical excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure a crystalline form of psilacetin according to the disclosure, specifically crystalline 4-acetoxy-N,N-dimethyltryptammonium hydrofumarate, the fumarate salt of psilacetin or crystalline bis(4-acetoxy-N,N-dimethyltryptammonium) fumarate, may be used as the "first purified psilocybin derivative" in the compositions described in US 2018/0221396 A1 and US 2019/0142851 A1. Exemplary psilocybin derivatives include but are not limited to psilocybin itself and the psilocybin derivates described in paragraphs [0081]-[0109] of US 2018/0221396 A1 and [082]-[0110] US 2019/0142851 A1 as well as the disclosed preferred embodiments. Exemplary cannabinoids include but are not limited to the cannabinoids described in paragraphs [0111]-[0159] of US 2018/0221396 A1 and [0112]-[0160] US 2019/0142851 A1 as well as the disclosed preferred embodiments. Exemplary terpenes include but are not limited to the terpenes described in paragraphs [0160]-[0238] of US 2018/0221396 A1 and [0161]-[0300] US 2019/0142851 A1 as well as the disclosed preferred embodiments. Accordingly, the disclosure provides a composition comprising as a first component: a crystalline form of psilacetin according to the disclosure, specifically crystalline 4-acetoxy-N,N-dimethyltryptammonium hydrofumarate, the fumarate salt of psilacetin or crystalline bis(4-acetoxy-N,N-dimethyltryptammonium) fumarate; and as a second component selected from (a) a purified psilocybin derivative, (b) one or two purified cannabinoids and (c) a purified terpene; with the rest being at least one suitable pharmaceutical excipient or at least one other adjuvant, as discussed below. Such a composition may be a pharmaceutical composition wherein the components are present individually in therapeutic effective amounts or by combination in a therapeutically effective amount to treat a disease, disorder or condition as described herein.

An "effective amount" or a "therapeutically effective amount" of a crystalline form of psilacetin according to the disclosure is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. A crystalline form of psilacetin according to the disclosure, compositions and pharmaceutical compositions containing it may be used in combination with other agents that are generally administered to a patient being treated for psychological and other disorders discussed above. They may also be co-formulated with one or more of such agents in a single pharmaceutical composition.

Depending on the type of composition or pharmaceutical composition, the excipient or pharmaceutically acceptable carrier may be chosen from any one or a combination of carriers known in the art. The choice of the pharmaceutically acceptable carrier depends upon the pharmaceutical form and the desired method of administration to be used. Preferred carriers include those that do not substantially alter the crystalline form of psilacetin or produce undesirable biological effects or otherwise interact in a deleterious manner with any other component(s) of the pharmaceutical composition.

The compositions or pharmaceutical compositions of the disclosure may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, the crystalline form of psilacetin may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Excipients or pharmaceutically acceptable adjuvants known in the formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a composition or a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of a crystalline form of psilacetin according to the disclosure in pure form, with a permeation enhancer, with stabilizers (e.g. antioxidants), or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, liquid dosage forms, such as, for example, tablets, suppositories, pills, soft elastic and hard gelatin capsules, powders, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

EXAMPLES

Single Crystal X-Ray Diffraction (SCXRD) Characterization: Data were collected on a Bruker D8 Venture CMOS Diffractometer equipped with an Oxford Cryosystems Cryostream cooling device and using Mo Kα radiation. Structures were solved using the Bruker SHELXTL program and refined with the SHELXTL program as part of the Bruker SHELXTL suite, or OLEX2 software. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Example 1: Preparation and Characterization of 4-Acetoxy-N,N-Dimethyltryptamine Hydrofumarate, Psilacetin Fumarate Crystal Preparation A commercial sample (The Indole Shop, Canada) of 4-acetoxy-N,N-dimethyltryptamine hydrofumarate was used for crystallization. Colorless crystals were grown by slow evaporation of an aqueous solution.

Single Crystal X-Ray Diffraction (SCXRD) Characterization

The single crystal data and structure refinement parameters for the crystalline structure measured at 296 K are reported in Table 1, below. The structure solution was obtained by intrinsic phasing. All non-hydrogen atoms were refined anisotropically (SHELXL) by full matrix least squares on $F^2$. Hydrogen atoms H1, H2, and H6a were found from Fourier difference maps and refined isotropically with 1.50 $U_{eq}$ of parent N or O atoms. All other hydrogens were placed in calculated positions with appropriate carbon-hydrogen bond lengths and: C—H(Ar) 0.930 Å, $CH_2$ 0.970 Å an $CH_3$ 0.960 Å and 1.20, 1.20 and 1.50 $U_{eq}$ of parent C atoms.

TABLE 1

| Crystal Data | |
|---|---|
| Empirical Formula | $C_{18}H_{22}N_2O_6$ |
| Formula weight | 362.37 |
| Temperature (K) | 296 |
| Crystal System, space group | monoclinic, $P2_1/c$ |
| a, b, c (Å) | 13.023 (1), 7.4823 (6), 19.102 (2) |
| α, β, γ (°) | 90, 103.251 (3), 90 |
| V(Å$^3$) | 1811.8 (3) |
| Z | 4 |
| Radiation Type | Mo Kα (λ = 0.71073) |
| μ (mm$^{-1}$) | 0.100 |
| F (000) | 768.0 |
| Crystal size (mm$^3$) | 0.27 × 0.22 × 0.20 |
| Data collection | |
| Diffractometer | Bruker D8 Venture CMOS |
| Absorption correction | Multi-scan |
| Reflections collected | 43099 |
| Independent reflections | 3320 [$R_{int}$ = 0.0366, $R_{sigma}$ = 0.0144] |

TABLE 1-continued

Crystal Data

| | |
|---|---|
| Data/restraints/parameters | 3320/0/251 |
| Goodness-of-fit on $F^2$ | 1.037 |
| Final R indexes [1 ≥ 2σ (1)] | $R_1$= 0.0419, $wR_2$ = 0.1024 |
| Final R indexes [all data] | $R_1$= 0.0522, $wR_2$ = 0.1118 |
| Largest diff. peak/hole (e Å$^{-3}$) | 0.34/-0.24 |

Computer programs: APEX3, SAINT, SADABS, SHELXS97, SHELXL2014, OLEX2

FIG. 1 shows the molecular structure of 4-acetoxy-N,N-dimethyltryptammonium hydrofumarate, the fumarate salt of psilacetin, with atoms labeled. Displacement ellipsoids are drawn at the 50% probability level. The asymmetric unit contains one 4-acetoxy-N,N-dimethyltryptammonium cation and one 3-carboxyacrylate anion. The indole of the cation is near planar with a mean deviation from planarity of 0.011 Å. The acetate unit is positioned in a perpendicular fashion, with the angle between the indole and acetate planes being 92.75(6)°. The singly protonated fumarate is in the trans configuration and is also nearly planar with a mean deviation from planarity of 0.053 Å. The ions are held together in the solid state through a series of hydrogen bonds (vide infra).

Figure 2:
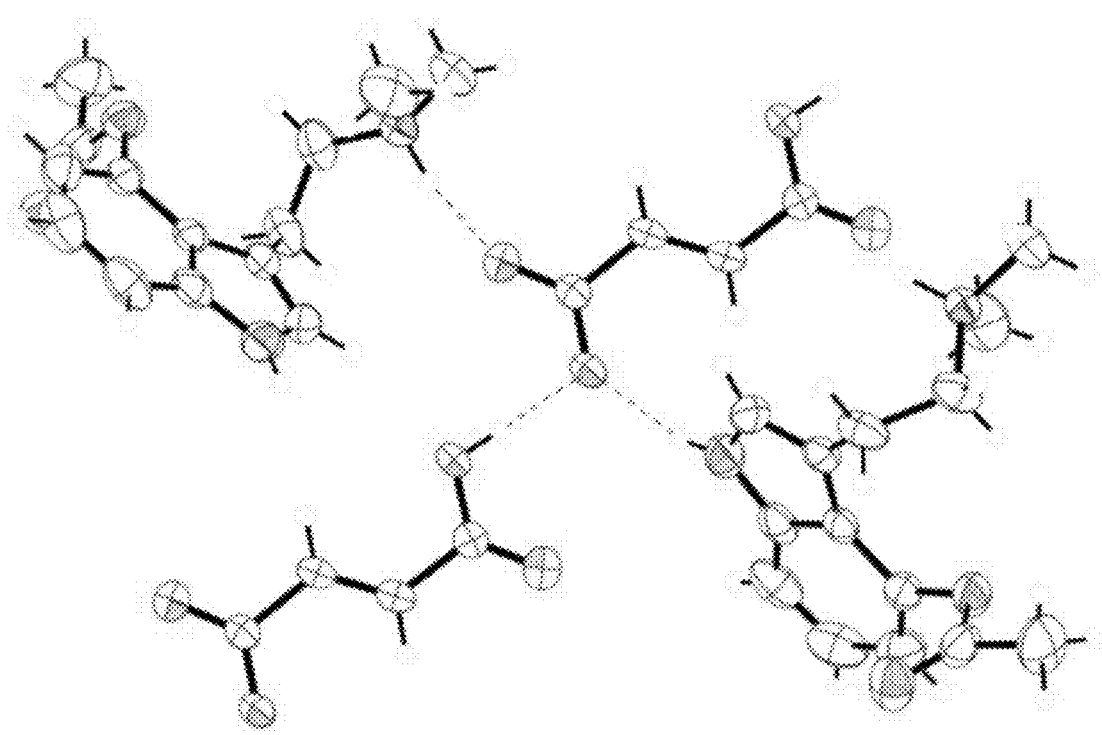
FIG. 2 shows the hydrogen bonding of the fumarate anion in the structure of 4-acetoxy-N,N-dimethyltryptammonium hydrofumarate.

FIG. 2 shows the hydrogen bonding of the fumarate anion in the structure of 4-acetoxy-N,N-dimethyltryptammonium hydrofumarate. The acetate end of the fumarate has three hydrogen bonds—one with an ammonium hydrogen, one with an indole hydrogen and one with the carboxylic acid hydrogen of another fumarate. The 4-acetoxy-N,N-dimethyltyptamine and fumarate ions are linked together into infinite chains along the [010] direction through N—H . . . O and O—H . . . O hydrogen bonds. One oxygen of the carboxylate on the 3-carboxyacrylate ion forms a hydrogen bond with the proton on the ammonium salt of a psilacetin molecule. The other oxygen of the carboxylate forms a hydrogen bond with an indole hydrogen, and also forms a hydrogen bond with the carboxylic acid of another fumarate ion (FIG. 2).

Figure 3:
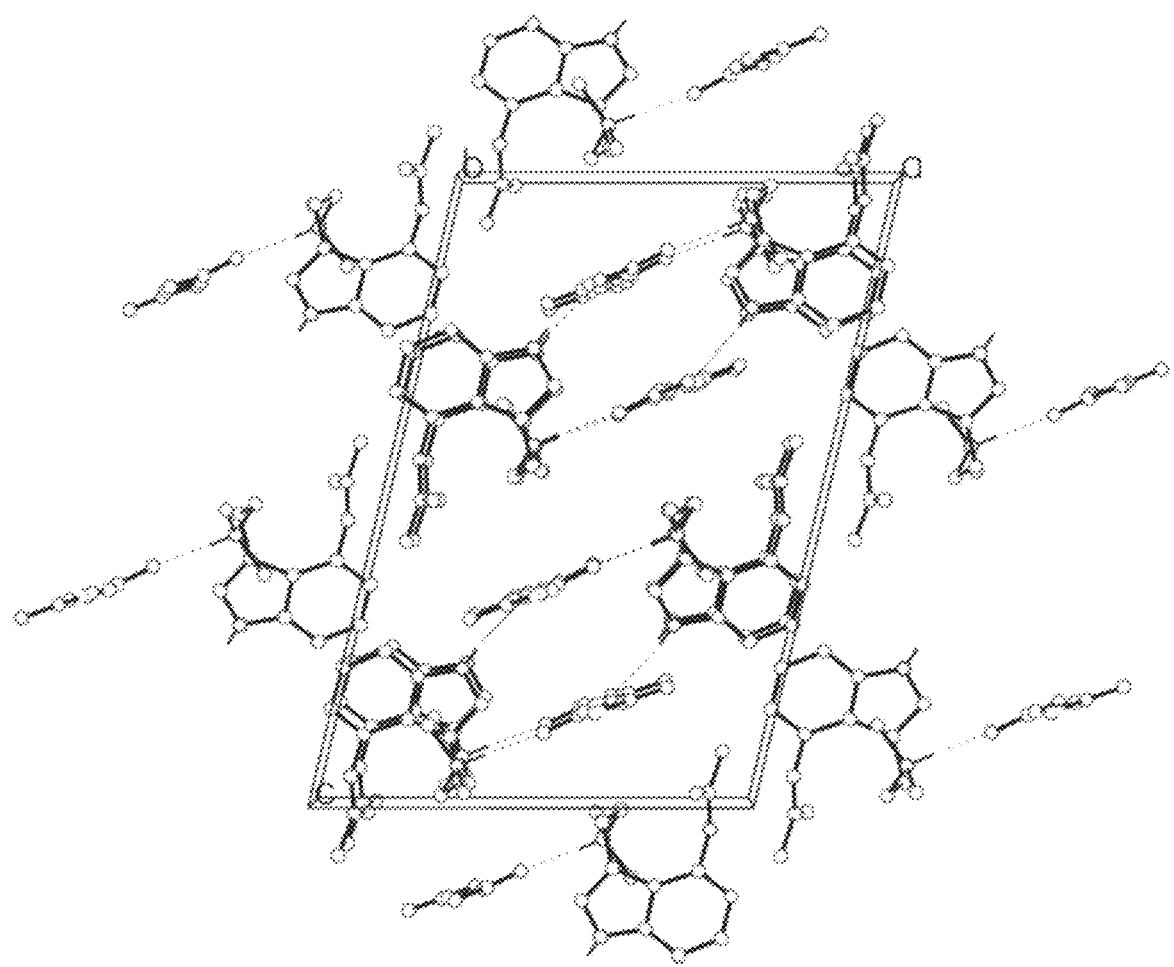
FIG. 3 shows the crystal packing of 4-acetoxy-N,N-dimethyltryptammonium hydrofumarate, viewed along the b axis.

FIG. 3 shows the crystal packing of 4-acetoxy-N,N-dimethyltryptammonium hydrofumarate, viewed along the b axis. The N—H . . . O and O—H . . . O hydrogen bonds are shown as dashed lines. Hydrogen atoms not involved in H-bonding have been removed for clarity.

Figure 4:
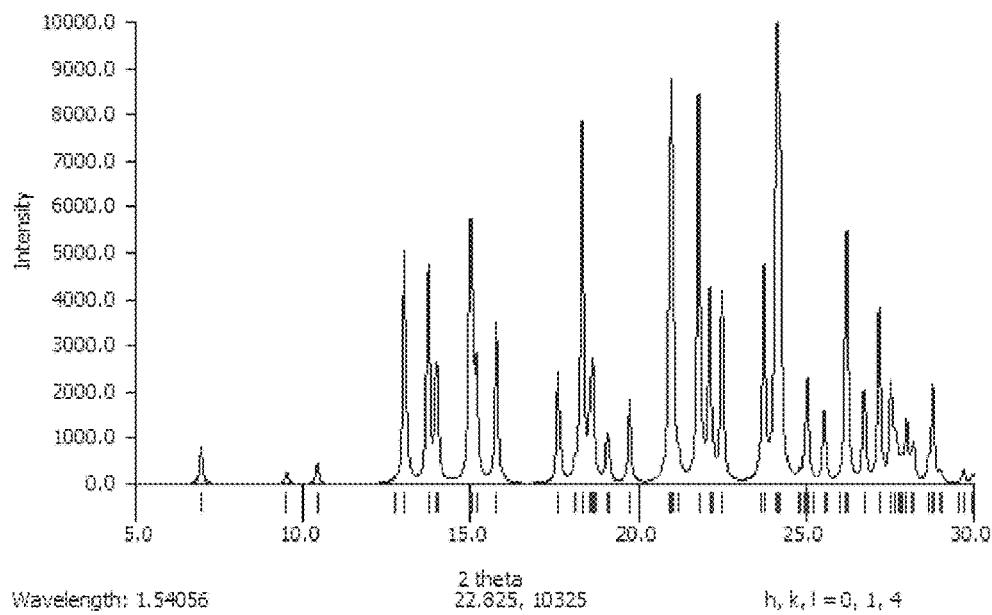
FIG. 4 is a simulated X-ray powder diffraction pattern (XRPD) for 4-acetoxy-N,N-dimethyltryptammonium hydrofumarate generated from its single crystal data.

FIG. 4 is a simulated X-ray powder diffraction pattern (XRPD) for 4-acetoxy-N,N-dimethyltryptammonium hydrofumarate generated from its single crystal data. Characteristic peaks identifying this crystalline form include peaks at 7.0, 13.0 and 21.8°2θ±0.2°2θ.

Example 2: Preparation and Characterization of bis(4-acetoxy-N,N-dimethyltryptammonium) fumarate Crystal Preparation A commercial sample (The Indole Shop) of 4-acetoxy-N,N-dimethyltryptamine hydrofumarate (100 mg, 0.16 mmol) was dissolved in 10 mL of water and treated with one equivalent of lead(II) acetate (53 mg, 0.16 mmol). Lead(II) fumarate precipitated and was filtered [the presence of lead(II) fumarate was confirmed by the unit cell of the precipitate]. Water was removed in vacuo and the resulting residue was picked up in acetone and filtered. The filtrate was allowed to evaporate slowly, resulting in single crystals suitable for X-ray analysis.

The single crystal data and structure refinement parameters for the crystalline structure measured at 296 K are reported in Table 2, below.

TABLE 2

Crystal Data

| | |
|---|---|
| Chemical Formula | $2C_{14}H_{19}N_2O_2^+ \cdot C_4H_2O_4^{2-}$ |
| $M_r$ | 608.68 |
| Crystal System, space group | Triclinic, P1 |
| Temperature (K) | 200 |
| a, b, c (Å) | 8.3965 (13), 8.9879 (14), 12.0126 (16) |
| α, β, γ (°) | 101.730 (5), 100.818 (5), 112.463 (5) |
| V(Å$^3$) | 784.2 (2) |
| Z | 2 |
| Radiation Type | Mo Kα |
| μ (mm$^{-1}$) | 0.09 |
| Crystal size (mm) | 0.19 × 0.16 × 0.13 |
| Data collection | |
| Diffractometer | Bruker D8 Venture CMOS |
| Absorption correction | Multi-scan SADABS2016/2 (Bruker, 2016/2) was used for absorption correction. wR2 (int) was 0.0632 before and 0.0573 after correction. The Ratio of minimum to maximum transmission is 0.9575. The λ/2 correction factor is Not present. |
| $T_{min}$, $T_{max}$ | 0.714, 0.745 |
| No. of measured, independent and observed [1 > 2σ(1)] reflections | 21581, 2877, 2087 |
| $R_{int}$ | 0.056 |
| (sin θ/λ)$_{max}$ (Å$^{-1}$) | 0.604 |
| Refinement | |
| R[$F^2$ > 2σ ($F^2$)], wR ($F^2$), S | 0.045, 0.110, 1.03 |
| No. of reflections | 2877 |
| No. of parameters | 210 |
| H-atom treatment | H atoms treated by a mixture of independent and constrained refinement |
| Δρ$_{max}$, Δρ$_{min}$ (e Å$^{-3}$) | 0.26, -0.20 |

Computer programs: SAINTV8.38A (Bruker-AXS, 2016), SHELXT2014/5 (Sheldrick, 2014), XL(Sheldrick, 2008), Olex2 (Dolomanov et al., 2009).

Single Crystal X-Ray Diffraction (SCXRD) Characterization

Figure 5:
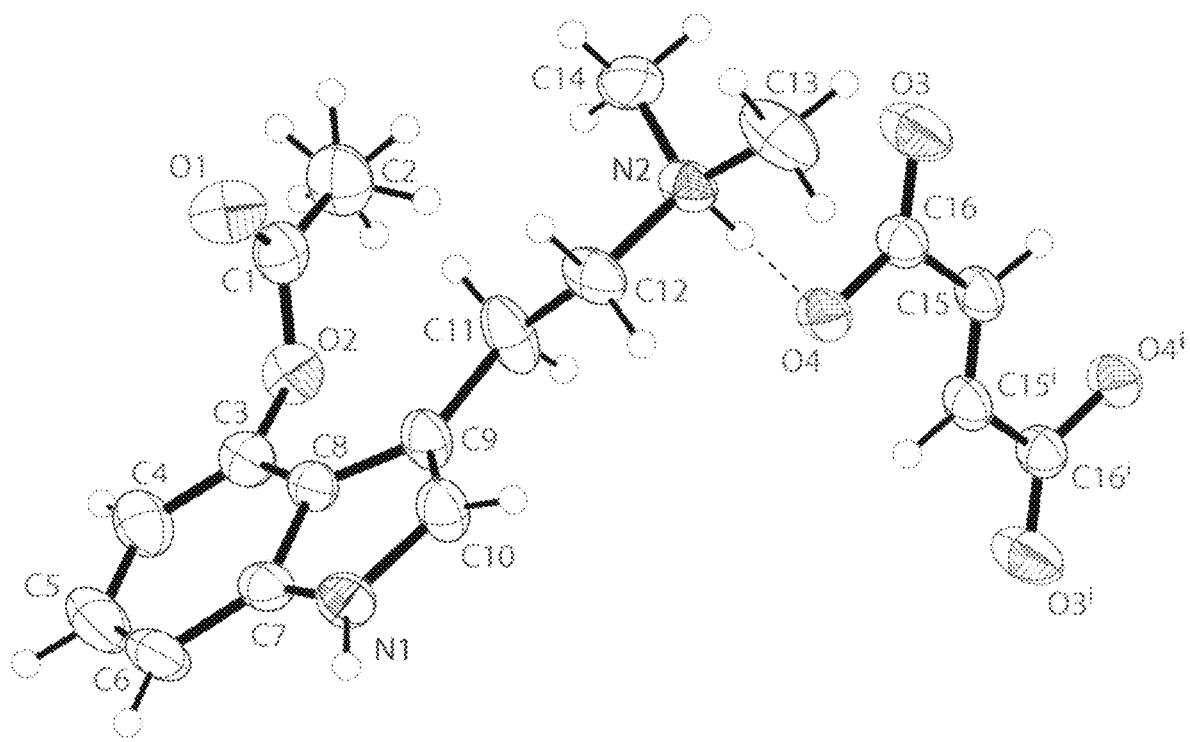
FIG. 5 shows the molecular structure of bis(4-acetoxy-N,N-dimethyltryptammonium) fumarate, showing the atomic labeling.

FIG. 5 shows the molecular structure of bis(4-acetoxy-N,N-dimethyltryptammonium) fumarate, showing the atomic labeling. Displacement ellipsoids are drawn at the 50% probability level. Hydrogen bonds are shown as dashed lines. Symmetry code: (i) 2-x, 1-y, 2-z. The cation possesses a near-planar indole, with a mean deviation from planarity of 0.04 Å. The acetate on the 4-position of the indole is approximately perpendicular, with the angles between the indole and acetate planes being 100.85 (1)°. Half of a fumarate ion is present in the asymmetric unit, with the full dianion produced through inversion. The fumarate shows a near planar trans configuration with a deviation from planarity of 0.019 Å. A series of N—H - - - O hydrogen bonds hold the ions together in the solid state.

Figure 6:
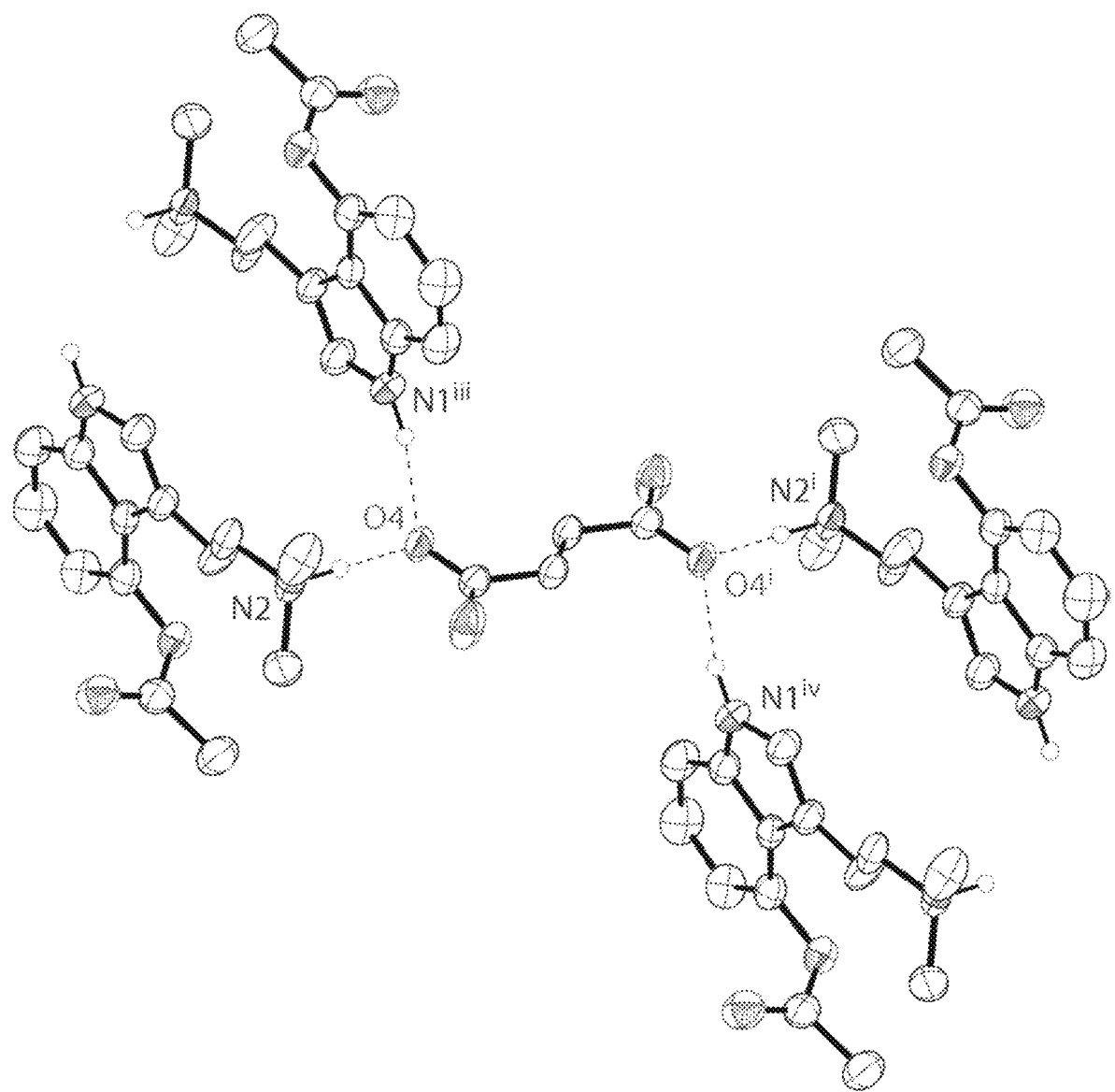
FIG. 6 shows the molecular structure of bis(4-acetoxy-N,N-dimethyltryptammonium) fumarate, showing the atomic labeling.

FIG. 5 shows the molecular structure of bis(4-acetoxy-N,N-dimethyltryptammonium) fumarate, showing the atomic labeling. Displacement ellipsoids are drawn at the 50% probability level. Hydrogen bonds are shown as dashed lines. Symmetry code: (i) 2-x, 1-y, 2-z. The 4-acetoxy-N,N-dimethyltryptammonium cations and fumarate dianions are held together in an infinite one dimensional chain through N—H - - - O hydrogen bonds along the [111] direction. The anionic oxygen of the carboxylic acid possesses a hydrogen bond with the ammonium proton of the psilacetin molecule. Each of these oxygens also forms a hydrogen bond with the hydrogen of an indole nitrogen of a different psilacetin cation. Both anionic oxygens of the fumarate dianions form the same hydrogen-bonding interactions, generated through symmetry. The hydrogen bonding interactions of a single fumarate dianion are shown in FIG. 6.

Figure 7:
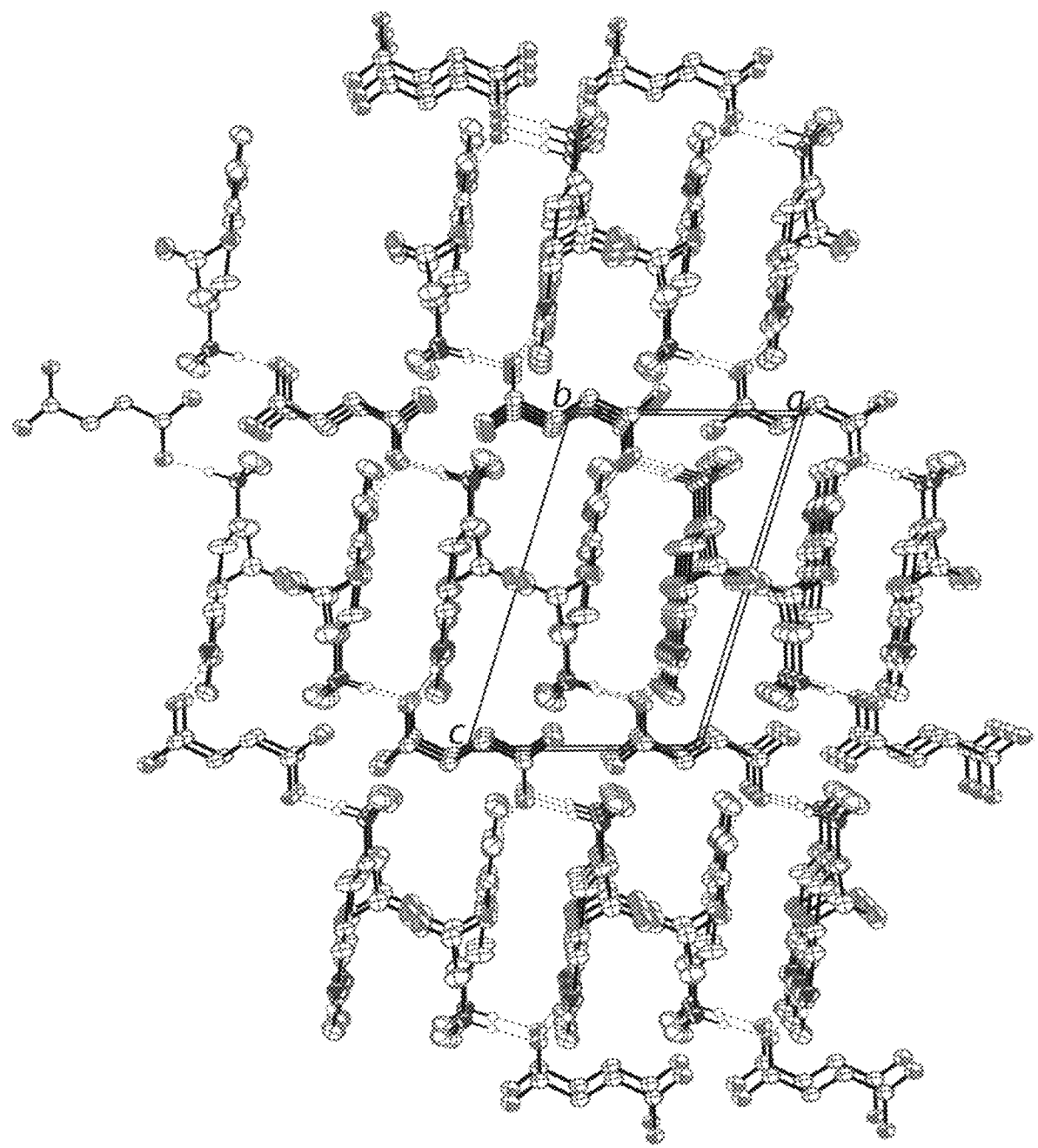
FIG. 7 shows the crystal packing of bis(4-acetoxy-N,N-dimethyltryptammonium) fumarate, viewed along the b axis.

FIG. 7 shows the crystal packing of bis(4-acetoxy-N,N-dimethyltryptammonium) fumarate, viewed along the b axis. The N—H - - - O bonds are shown as dashed lines. Displacement ellipsoids are drawn at the 50% probability level. Hydrogen atoms not involved in hydrogen bonding are omitted for clarity.

Figure 8:
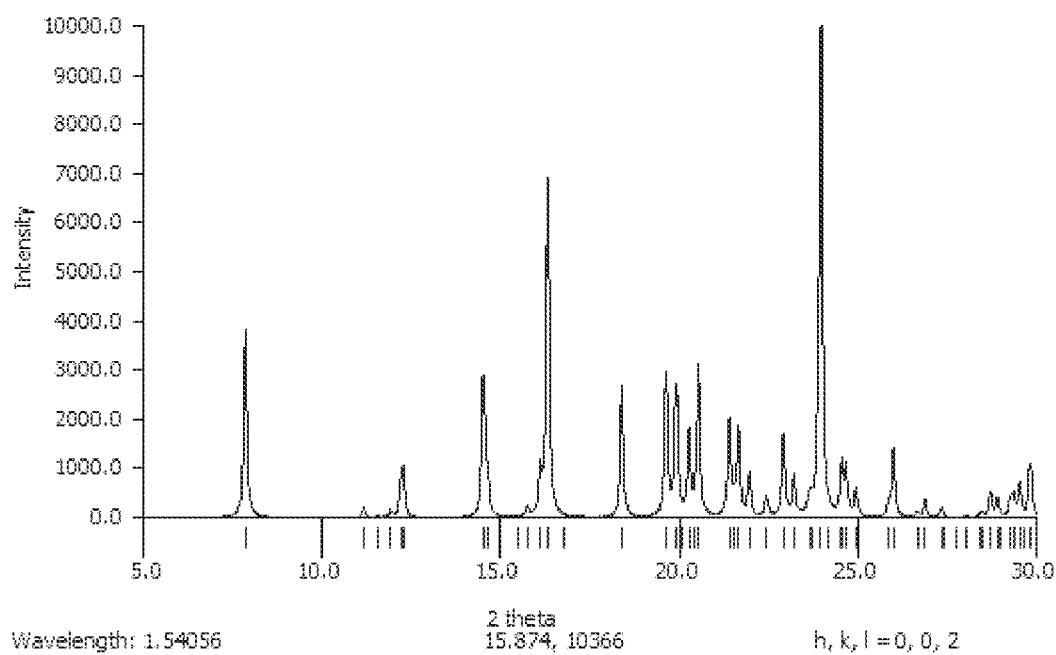
FIG. 8 is a simulated X-ray powder diffraction pattern (XRPD) for bis(4-acetoxy-N,N-dimethyltryptammonium) fumarate generated from its single crystal data.

FIG. 8 is a simulated X-ray powder diffraction pattern (XRPD) for bis(4-acetoxy-N,N-dimethyltryptammonium) fumarate generated from its single crystal data. Characteristic peaks identifying this crystalline form include peaks at 7.9, 18.4 and 24.0°2θ±0.2°2θ.

REFERENCES

1. Bruker (2016). APEX3, SAINT, and SADABS. Bruker AXS Inc., Madison, Wis., USA.
2. Carhart-Harris, R. L.; Goodwin, G. M. "The Therapeutic Potential of Psychedelic Drugs: Past, Present, and Future" *Neuropsychopharmacology*, 2017, 42, 2105-2113.
3. Chadeayne, A. R., Golen, J. A. & Manke, D. R. (2019). Psychedelic Science Review, https://psychedelicreview.com/the-crystal-structure-of-4-aco-dmt-fumarate/.
4. Dinis-Oliveira, R. J. (2017). Drug Metab. Rev. 49, 84-91.
5. Dolomanov, O. V.; Bourhis, L. "OLEX2: a complete structure solution, refinement and analysis program" *Journal of Applied Crystallography*, 2009, 42, 339-341.
6. Gilman, A.; Hardman, J.; Limbird L., eds., Goodman and Gilman's "The Pharmacological Basis of Therapeutics," Tenth Edition, McGraw-Hill Press, 155-173 (2001).
7. Nichols, D. E.; Frescas, S. "Improvements to the Synthesis of Psilocybin and a Facile Method for Preparing the OAcetyl Prodrug of Psilocin" *Synthesis*, 1999, 6, 935-938.
8. Petcher, T. J.; Weber, H. P. "Crystal Structure of the Teonanácatl Hallucinogens. Part II. Psilocin, $C_{12}H_{15}N_2O$" *Journal of the Chemical Society, Perkins Transactions II*, 1974, 946-948.
9. Bruker 2016 APEX3, SAINT and SADABS. Bruker AXS Inc., Madison, Wis., USA.
10. Sheldrick, G. M. "A short history of SHELX" *Acta Crystallographica Section A: Foundations and Advances*, 2008, 64, 112-122.
11. Sheldrick, G. M. "Crystal structure refinement with SHELXL" *Acta Crystallographica Section C: Structural Chemistry*, 2015, 71, 3-8.
12. Weber, H. P.; Petcher, T. J. "Crystal Structure of the Teonanácatl Hallucinogens. Part I. Psilocybin $C_{12}H_{17}N_2O_4P$" *Journal of the Chemical Society, Perkins Transactions II*, 1974, 942-946.

The claimed invention is:

1. Crystalline bis(4-acetoxy-N,N-dimethyltryptammonium) fumarate.
2. Crystalline bis(4-acetoxy-N,N-dimethyltryptammonium) fumarate according to claim 1 characterized by:
   a triclinic, P1 crystal system space group at a temperature of about 200 K,
   unit cell dimensions a=8.3965 (13) Å, b=8.9879 (14) Å, c=12.0126 (16) Å, α=101.730 (5)°, β=100.818 (5)°, and γ=112.463 (5)° at a temperature of about 200 K;
   an x-ray powder diffraction pattern substantially similar to FIG. 8; or
   an x-ray powder diffraction pattern characterized by peaks at 7.9, 18.4 and 24.0°2θ±0.2°2θ.
3. A composition comprising crystalline bis(4-acetoxy-N,N-dimethyltryptammonium) fumarate according to claim 1 and an excipient.
4. A composition comprising as crystalline bis(4-acetoxy-N,N-dimethyltryptammonium) fumarate and a second component selected from (a) a purified psilocybin derivative, (b) one or two purified cannabinoids and (c) a purified terpene.
5. Bis(4-acetoxy-N,N-dimethyltryptammonium) fumarate.
6. A method of preventing or treating a psychological disorder comprising the step of:
   administering to a subject in need thereof a therapeutically effective amount of crystalline bis(4-acetoxy-N,N-dimethyltryptammonium) fumarate according to claim 1.
7. A method of preventing or treating a psychological disorder comprising the step of:
   administering to a subject in need thereof a therapeutically effective amount of crystalline bis(4-acetoxy-N,N-dimethyltryptammonium) fumarate according to claim 2.
8. A method of preventing or treating a psychological disorder comprising the step of:
   administering to a subject in need thereof a composition according to claim 3.
9. A method of preventing or treating inflammation and/or pain comprising the step of:
   administering to a subject in need thereof a therapeutically effective amount of crystalline bis(4-acetoxy-N,N-dimethyltryptammonium) fumarate according to claim 1.
10. A method of preventing or treating inflammation and/or pain comprising the step of:
    administering to a subject in need thereof a therapeutically effective amount of crystalline bis(4-acetoxy-N,N-dimethyltryptammonium) fumarate according to claim 2.
11. A method of preventing or treating inflammation and/or pain comprising the step of:
    administering to a subject in need thereof a composition according to claim 3.

* * * * *